US005894017A

United States Patent [19]
Sagel et al.

[11] Patent Number: 5,894,017
[45] Date of Patent: Apr. 13, 1999

[54] DELIVERY SYSTEM FOR AN ORAL CARE SUBSTANCE USING A STRIP OF MATERIAL HAVING LOW FLEXURAL STIFFNESS

[75] Inventors: Paul A. Sagel, Mason; Robert S. Dirksing, Cincinnati; Frederick J. Rohman, Maineville, all of Ohio

[73] Assignee: The Procter & Gamble Company, Cincinnati, Ohio

[21] Appl. No.: 08/870,664

[22] Filed: Jun. 6, 1997

[51] Int. Cl.$^6$ ............................ A61K 6/02; A61K 7/16; A61K 7/20
[52] U.S. Cl. ........................ 424/401; 424/49; 424/53; 433/215
[58] Field of Search ........................ 433/215; 424/401, 424/49-58

[56] References Cited

U.S. PATENT DOCUMENTS

| | | | |
|---|---|---|---|
| Re. 33,093 | 10/1989 | Schiraldi et al. | 424/676 |
| 2,835,628 | 5/1958 | Saffir | 167/84 |
| 3,688,406 | 9/1972 | Porter et al. | 32/40 R |
| 3,754,332 | 8/1973 | Warren, Jr. | 32/64 |
| 3,955,281 | 5/1976 | Weitzman | 32/14 |
| 4,138,814 | 2/1979 | Weitzman | 32/14 |
| 4,307,075 | 12/1981 | Martin | 424/28 |
| 4,324,547 | 4/1982 | Arcan et al. | 433/71 |
| 4,713,243 | 12/1987 | Schiraldi et al. | 424/151 |
| 4,728,291 | 3/1988 | Golub | 433/215 |
| 4,741,700 | 5/1988 | Barabe | 433/229 |
| 4,741,941 | 5/1988 | Englebert et al. | 428/71 |
| 4,786,253 | 11/1988 | Morais | 433/60 |
| 4,799,888 | 1/1989 | Golub | 433/215 |
| 4,900,552 | 2/1990 | Sanvordeker | 424/422 |
| 4,900,554 | 2/1990 | Yanagibashi et al. | 424/448 |
| 4,919,615 | 4/1990 | Croll | 433/3 |
| 5,098,303 | 3/1992 | Fischer | 433/215 |
| 5,166,233 | 11/1992 | Kuroya et al. | 524/37 |
| 5,234,342 | 8/1993 | Fischer | 433/215 |
| 5,310,563 | 5/1994 | Curtis et al. | 424/616 |
| 5,326,685 | 7/1994 | Gagli. et al. | 433/215 |
| 5,340,314 | 8/1994 | Tarvis | 433/168.1 |
| 5,380,198 | 1/1995 | Suhonen | 433/39 |
| 5,409,631 | 4/1995 | Fischer | 252/186 |
| 5,425,953 | 6/1995 | Sintov et al. | 424/404 |
| 5,438,076 | 8/1995 | Friedman et al. | 514/772 |
| 5,560,379 | 10/1996 | Pieczenik | 132/329 |
| 5,575,654 | 11/1996 | Fontenot | 433/215 |
| 5,611,687 | 3/1997 | Wagner | 433/80 |
| 5,620,322 | 4/1997 | Lococo | 433/39 |
| 5,626,866 | 5/1997 | Ebert et al. | 424/447 |
| 5,639,445 | 6/1997 | Curtis et al. | 424/49 |
| 5,707,736 | 1/1998 | Levey et al. | 428/375 |
| 5,713,738 | 2/1998 | Yarborough | 433/215 |

FOREIGN PATENT DOCUMENTS

| | | | |
|---|---|---|---|
| 0763358A1 | 3/1997 | European Pat. Off. | A61K 9/70 |
| 63-54318 | 3/1988 | Japan | A61K 9/70 |
| 10-17448 | 1/1998 | Japan | A61K 7/16 |
| 2075965-C1 | 3/1997 | Russian Federation | A61C 13/23 |
| 1142325 | 5/1969 | United Kingdom . | |
| 2 108841 | 5/1983 | United Kingdom | A61K 9/24 |
| WO 95/05416 | 2/1995 | WIPO | C08L 1/26 |

OTHER PUBLICATIONS

U.S. application No. 08/870,665, Dirksing et al., filed Jun. 6, 1997.
U.S. application No. 08/870,331, Dirksing et al., filed Jun. 6, 1997.
U.S. application No. 08/870,330, Sagel et al., filed Jun. 6, 1997.
U.S. application No. 08/870,664, Sagel et al., filed Jun. 6, 1997.
"Plastic Films" by J.H. Briston, 1974, pp. 96–97.
"Tray–Forming Technique for Dentist–Supervised Home Bleaching" by S.M. Newman et al., Quintessence International vol. 26, No. 7/0/1995, pp. 447–453.
"Color Atlas of Tooth Whitening" By G. McLaughlin et al., 1991, pp. 35–38 and 45–50.
"Complete Dental Bleaching" By R.E. Goldstein et al., 1995, pp. 25–32 and 90–97.

*Primary Examiner*—Shep K. Rose
*Attorney, Agent, or Firm*—Angela Marie Stone; Betty J. Zea; Ronald W. Kock

[57] ABSTRACT

A delivery system for an oral care substance includes a strip of material having a flexural stiffness less than about 50 grams/centimeter as measured on a Handle-O-Meter per ASTM test method D2923-95. The strip of material is readily conformable without permanent deformation to a shape of a tooth and its adjoining soft tissue when the delivery system is placed thereagainst. The delivery system also includes an oral care substance applied to the strip of material such that when the delivery system is placed on a surface of the tooth and its adjoining soft tissue, the substance contacts the surface providing an active onto the surface. The substance also provides adhesive attachment between the strip of material and the surface to hold the delivery system in place for a sufficient time to allow the active to act upon the surface. A method of delivery includes pre-coating the strip of material, having the wearer apply substance to the strip of material, or having the wearer apply the substance directly to the surface before applying a strip of material.

21 Claims, 1 Drawing Sheet

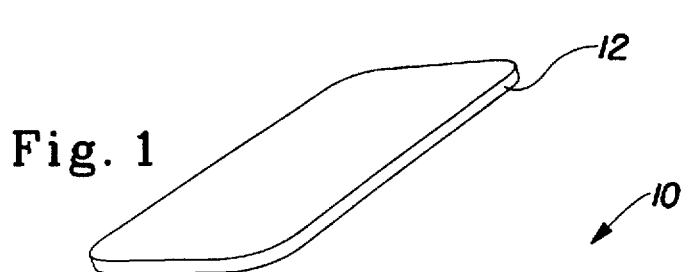
Fig. 1
Fig. 2
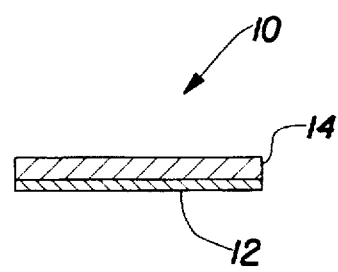
Fig. 3
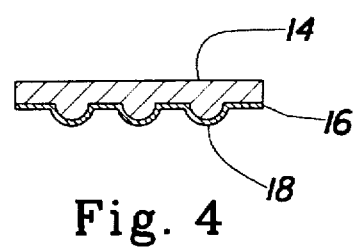
Fig. 4
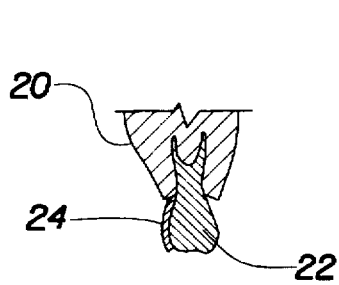
Fig. 5
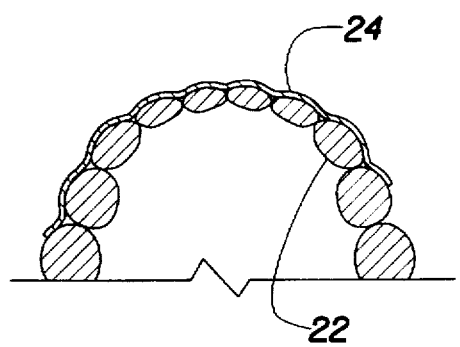
Fig. 6
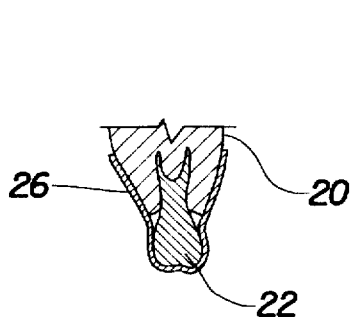
Fig. 7
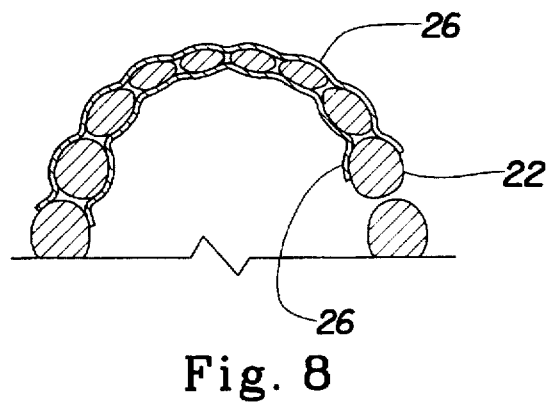
Fig. 8

DELIVERY SYSTEM FOR AN ORAL CARE SUBSTANCE USING A STRIP OF MATERIAL HAVING LOW FLEXURAL STIFFNESS

FIELD OF THE INVENTION

The present invention relates to a system for the delivery of an oral care substance to one's oral tissue, a surface of a tooth, a number of adjacent teeth, or a combination thereof, and more particularly to such delivery system wherein the substance is protected from erosion within the mouth for a time sufficient to enable an active provided by the substance to provide a therapeutic benefit. Even more particularly, the present invention relates to disposable delivery systems used outside a dentist office, wherein such delivery systems are inexpensive and unobtrusive so as to be wearable without interfering with normal social discourse.

BACKGROUND OF THE INVENTION

The most common implement for dental hygiene is the toothbrush. The mechanical action of the toothbrush bristles aids in the removal of food particles, plaque, and the like. The toothbrush is normally used with a toothpaste. Prior to about 1955, a typical toothpaste consisted of a surfactant and an abrasive material. These products were simply intended to augment the mechanical action of the brushing.

In 1955, CREST® toothpaste with fluoride, a Trademark of The Procter & Gamble Company of Cincinnati, Ohio, was introduced and the toothbrush and fluoride toothpaste combination proved to be a suitable means to deliver a fluoride treatment to the teeth surfaces. Subsequently, other active ingredients, such as tartar control agents, have been added to toothpaste to provide further dental hygiene benefits. Consumers have also turned their attention to the cosmetic aspects of dental care, such as teeth straightening and whitening.

Given the success of delivering chemicals which provide therapeutic benefits for oral care, it is reasonable to expect similar success in accomplishing the cosmetic benefit via routine brushing. For example, products have been introduced which claim to whiten teeth. However, in spite of the claims, the combination of the low allowable strength of the orally used chemicals and the significant contact time necessary for whitening to occur effectively prevents significant whitening via a regular program of brushing. As a consequence, people who are serious about whitening their teeth and who have been disappointed by the results of whitening dentifrices, often resort to professional help for whitening their teeth.

Professional teeth whitening programs provided by dentists generally fall into two categories: an in-office bleaching procedure and an outside-the-office bleaching procedure. The in-office procedure involves several visits, each of which begins with the fabrication of a specially fitted rubber dam within the mouth to prevent the bleaching chemicals, typically hydrogen peroxide, from contacting the soft oral tissue. The production of the rubber dam within the patient's mouth may be both painful and time consuming. However, the strength of the peroxide bleach mandates the use of the dam. The in-office procedure may also leave the teeth sensitive to heat and cold and is very expensive.

The outside-the-office bleaching program differs in that the patient applies the bleaching agent to his or her own teeth using a lower strength chemical over an extended period of time, typically several hours a day for several weeks. The outside-the-office program typically requires an initial fitting in the dentist's office for an appliance which is specific to the particular patient. The appliance is a device that is fabricated to fit precisely onto the patient's teeth and is used to deliver to the patient's teeth a bleaching product, such as a gel containing urea/hydrogen peroxide complex. The patient is responsible for measuring and applying the bleaching agent to the surfaces of the teeth using the appliance as the means for delivery and containment.

Because the appliance is reused, it must be sufficiently robust to endure repeat handling, cleaning, filing, installation, and wearing. Such appliances are relatively rigid in order to maintain fit during repeat use. As a result, the edge of an appliance is generally stiff, often causing gum irritation; and its substantial thickness is usually apparent to both the wearer and others. Typically, a patient uses the device in time periods when social contact can be avoided.

There are now non-professional programs available to persons interested in whitening their teeth using commercial products available at drug stores. The commercial products provide a kit which includes a generic appliance and a container of bleaching gel. The obvious appeal is the lower cost of the program. A major disadvantage of this "one size fits all" appliance is the greater void between the interior walls of the appliance and the teeth versus the professionally fitted appliance. Hence, in order to insure intimate contact of the bleaching gel and the teeth surfaces, more bleaching gel is required. Furthermore, the poorer fit means a greater loss of bleaching gel onto the gums, into the oral cavity, and eventually ingested. The commercial kits, like the outside-the-office professionally administered program, require the user to clean and to reuse the appliance. Since generic appliances are not fitted to the individual user, they are even more bulky in the mouth than the fitted appliances and thus they restrict social discourse to a greater degree.

One attempt to remedy some of the problems of the commercial kits is disclosed in U.S. Pat. No. 5,575,654, issued to Fontenot on Nov. 19, 1996. Fontenot discloses a prepackaged moldable dental appliance, adapted to fit a wide range of variously sized dental arches, which contains a premeasured amount of medicinal or bleaching agent. In use, the dental appliance is removed from the packaging, aligned in a parallel fashion to the edges of the teeth and pushed over the teeth in the direction of the periodontal tissue until it covers the teeth surfaces. The primary benefit of the device disclosed by Fontenot is elimination of the measuring and filling of the appliance and the disposability after each use. However, it has been observed that the device frequently has the problems of bulk and compromised fit.

A second solution is disclosed in U.S. Pat. No. 5,310,563, issued to Curtis et al. on May 10, 1994. Curtis et al. disclose a putty-like material which is formed by pressing against the teeth. It is held in place by mechanical engagement with undercut surfaces and by friction. The composition encapsulates the active. The active migrates from the composition to the gums and tooth surfaces rather than being directly in contact with them. Presumably, the required wearing time is increased, which may be a significant negative.

What is needed is a low cost commercial delivery system, which has a customized fit for a minimal volume of an active providing substance, and which is in conformable contact with the appropriate oral surfaces for rapid delivery of the active. In addition a delivery system is needed which does not require extensive user placement manipulation to be certain of good contact. Furthermore, what is needed is a non-bulky active containment means that will permit the wearer to use the system during social discourse without interfering with the wearer's speech or appearance. Also

3 needed is a containment means that will protect the substance from erosion from contact with inner mouth surfaces.

SUMMARY OF THE INVENTION

In practicing the present invention, a strip of material is applied by the wearer to a portion of a tooth, to an entire tooth, or to a row of adjacent teeth. The side of the material facing the tooth is either coated with the substance or the teeth are coated with the substance and the strip of material is placed over the substance. In either case, the substance is preferably in a highly viscous state, such as a gel, such that it provides not only the active but also tackiness between the tooth surfaces and the strip of material to hold the strip of material in place. The conformable strip of material is preferably of a size that individually fits the entire upper or lower rows of teeth when positioned against the teeth. As a soft, conformable material, the strip may come into contact with the wearer's gums without causing irritation. The strip of material readily conforms to the teeth by lightly pressing it thereagainst and/or by the wearer gently sucking through the gaps between teeth. The strip of material is easily removed by the wearer after use by peeling it off. Each successive treatment uses a fresh strip of material.

By being a relatively thin coating, the substance is low in volume compared to the substance contained by rigid trays fitted or unfitted. Therefore, substance is not wasted, and little of it is accidentally ingested or otherwise available for irritation of oral cavity surfaces for which it is not intended. Preferably, the strip of material and substance are substantially transparent so as to be almost unnoticeable when worn. Thinness of the delivery system enables the higher temperature of the inside of the wearer's mouth to conduct heat through the strip of material to the normally cooler teeth in order to accelerate the rate of diffusion of the active material into the surface of the teeth.

In one aspect of the present invention, a delivery system for an oral care substance includes a strip of material having a flexural stiffness less than about 50 grams/centimeter as measured on a Handle-O-Meter, available from Thwing-Albert Instrument Co. of Philadelphia, Pa. The strip of material is readily conformable without permanent deformation to a shape of a tooth and its adjoining soft tissue when the delivery system is placed thereagainst. The delivery system also includes an oral care substance applied to the strip of material such that when the delivery system is placed on a surface of the tooth and its adjoining soft tissue, the substance contacts the surface providing an active onto the surface. The substance also provides adhesive attachment between the strip of material and the surface to hold the delivery system in place for a sufficient time to allow the active to act upon the surface.

Preferably, the substance is in the form of a gel, which is a substantially uniform continuous coating on the strip of material. The strip of material may have shallow pockets on a substance-coated side of the strip of material, such that the shallow pockets have substance located therein. The strip of material is preferably a piece of low density polyethylene film having a nominal film thickness of about 0.013 mm, which is substantially flat and rectangular in shape with rounded corners, and the strip of material including the substance applied thereon has an overall thickness less than about 1 mm. The strip of material may have a length sufficient to cover a plurality of adjacent teeth while conforming to the curvature of the wearer's mouth and gaps between the adjacent teeth. Ideally, the strip of material and the substance are substantially unnoticeable by others when worn.

4

In another aspect of the present invention, a method of delivering an oral care substance to a surface of a tooth and its adjoining soft tissue includes the step of applying the substance onto a conformable strip of material having a flexural stiffness less than about 50 grams/centimeter as measured on a Handle-O-Meter. Alternatively, this step could include applying the substance onto the surface of the tooth and its adjoining soft tissue. Another step is applying the conformable strip of material to the surface without permanent deformation of the strip of material. The substance provides an active onto the surface and also provides adhesive attachment between the strip of material and the surface to hold the delivery system in place for a sufficient time to allow the active to act upon the surface.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a perspective view of a substantially flat strip of material having rounded corners;

FIG. 2 is a perspective view of an embodiment of the present invention, disclosing the flat strip of FIG. 1 coated with an oral care substance;

FIG. 3 is a cross-section view thereof, taken along section line 3—3 of FIG. 2, disclosing the flat strip having a thickness less than that of the substance coated thereon;

FIG. 4 is a cross-section view showing an alternative embodiment of the present invention, showing shallow pockets in the strip of material, which act as reservoirs for additional substance coated on the strip;

FIG. 5 is a cross-section elevation view of a tooth and adjoining soft tissue, disclosing the strip of the present invention conforming to and adhesively attached to the tooth by means of the substance located between the tooth and the strip of material;

FIG. 6 is a cross-section plan view thereof, showing adjacent teeth having the strip of material of the present invention conforming thereto and adhesively attached to the teeth by means of a substance located between the teeth and the strip of material;

FIG. 7 is a cross-section elevation view, similar to FIG. 5, showing the strip of material of the present invention conforming to both the teeth and the adjoining soft tissue and adhesively attached to the teeth by means of the substance located between the teeth and the strip of material; and FIG. 8 is a cross-section plan view, similar to FIG. 6, showing a strip of material of the present invention conforming to the teeth and the adjoining soft tissue and adhesively attached to the teeth by means of the substance located between the teeth and the strip of material.

DETAILED DESCRIPTION OF THE INVENTION

Referring now to the drawings, and more particularly to FIGS. 1 and 2, there is shown a first preferred embodiment of the present invention, which is generally indicated as 10. Embodiment 10 represents a delivery system for an oral care substance. Delivery system 10 has a strip of material 12, which is initially substantially flat with rounded corners.

Strip of material 12 may be a single layer of polymer, woven, non-woven, foil, paper, rubber, or a combination thereof, such as a laminate.

Applied or coated onto strip of material 12 is an oral care substance 14. Preferably, substance 14 is a homogeneous fluid, uniformly and continuously coated onto strip of material 12, as shown in FIG. 3. However, substance 14 may alternatively be a laminate or separated layers of components, an amorphous mixture of components, separate stripes or spots or other patterns of different components, or a combination of these structures including a continuous coating of oral care substance 14 along a longitudinal axis of a portion of a strip of material 12.

Substance 14 preferably contains or is itself an active, such as a composition, compound, or mixture capable of influencing or effecting a desired change in appearance and/or structure of the surface it contacts. Example actives include: hydrogen peroxide, carbamide peroxide, sodium fluoride, sodium monofluorophosphate, pyrophosphate, chlorhexidine, polyphosphate, triclosan, and enzymes. Examples of appearance and structural changes include, but are not necessarily limited to: whitening, stain bleaching, stain removal, remineralization to form fluorapatite, plaque removal, and tartar removal.

As an alternative embodiment, a strip of material 16 may have shallow pockets 18 formed therein. When substance 14 is coated on a substance-coated side of strip of material 16, additional substance 14 fills shallow pockets 18 to provide reservoirs of additional substance 14, as shown in FIG. 4.

FIGS. 5 and 6 show a delivery system 24 of the present invention applied to a surface of a tooth or adjacent teeth. In adjoining soft tissue 20 is embedded a tooth 22. Tooth 22 is herein defined as a portion of a tooth, an individual tooth, or a set of adjacent teeth. FIG. 6 shows a set of adjacent teeth, for example. Adjoining soft tissue is herein defined as tissue surfaces surrounding the tooth structure including: marginal gingiva, gingival sulculus, inter dental gingiva, gingival gum structure on lingual and buccal surfaces up to and including muco-ginival junction and the pallet.

In both FIGS. 5 and 6, delivery system 24 represents strip of material 12 and substance 14, with substance 14 on the side of strip of material 12 facing tooth 22. Substance 14 may be pre-applied to strip of material 12, applied to strip of material 12 by the delivery system user, or applied directly to tooth 22 and then covered by strip of material 12. In any of these cases, strip of material 12 has a thickness and flexural stiffness which enable it to conform to the contoured surfaces of tooth 22 and to adjoining soft tissue 20.

Strip of material 12 serves as a protective barrier for substance 14 to substantially prevent leaching and/or erosion of substance 14 from the surface of tooth 22 by the wearer's lips, tongue, other soft tissue, and saliva contacting the substance. In order for an active in oral care substance 14 to act upon the surface of tooth 22 over an extended period of time, from several minutes to several hours, it is important to minimize such leaching and/or erosion. The term "act upon" is herein defined as bringing about a desired change. For example, if the substance is a peroxide, it bleaches color bodies inside the tooth to bring about whitening; or if the active is sodium fluoride, it promotes the formation of fluorapatite in an enamel matrix, turning the enamel matrix into a less acid soluble material.

Strip of material 12 is held in place on tooth 22 by adhesive attachment provided by substance 14. Strip of material 12 has a flexural stiffness less than about 50 grams/centimeter as measured on a Handle-O-Meter, model #211-300, available from Thwing-Albert Instrument Co. of Philadelphia, Pa., as per test method ASTM D2923-95. This relatively low stiffness enables strip of material 12 to drape over the contoured surfaces of tooth 22 with very little force being exerted. That is, conformity to the curvature of the wearer's mouth and gaps between adjacent teeth is maintained because there is little residual force within strip of material 12 to cause it to return to its substantially flat shape. The flexibility of the strip also enables strip of material 12 to contact adjoining soft tissue 20 over an extended period of time without irritation. This is in contrast to rigid and semi-rigid trays, even when fitted to the teeth, which are known to irritate the wearer's gums due to rubbing. Strips of material 12 having a flexural stiffness above this upper value are prone to loosen and become dislodged from their desired placement position. Strip of material 12 does not require pressure forming it against the tooth. It does not permanently deform like some prior art systems which require pressure to force a material to take the shape of the teeth, and which fit by permanent deformation rather than drape.

The viscosity and general tackiness of substance 14 cause strip of material 12 to be adhesively attached about tooth 22 without substantial slippage under the potential friction of lips and tongue and other soft tissue rubbing against strip of material 12 during mouth movements associated with talking, drinking, etc.

FIGS. 7 and 8 show a delivery system 26 of the present invention applied to a surface of tooth 22 as well as to adjoining soft tissue 20. Delivery system 26 represents strip of material 12 and substance 14, with substance 14 on the side of strip of material 12 facing tooth 22 and adjoining soft tissue 20. Although strip of material 26 may not be adhesively attached to adjoining soft tissue 20, it may be held in position by being adhesively attached to tooth 22.

In a particularly preferred embodiment of the present invention, substance 14 is a tooth whitening gel containing 30–85% glycerin or polyethylene glycol, 10–22% urea/hydrogen peroxide complex, 0–12% carboxypolymethylene, 0–1% sodium hydroxide, 0–10% triethanolamine (TEA), 0–40% water, 0–1% flavor, 0–15% sodium citrate, and 0–5% ethylenediaminetetraacetic acid. The preferred gel has a viscosity between 200 and 1,000,000 cps at low shear rates (less than one 1/seconds). Even more preferably, a tooth whitener is a gel containing 70% glycerin, 5% carboxypolymethylene, 10% carbamide peroxide, 15% water adjusted to pH 6.5 with sodium hydroxide. Commercial tooth whiteners, such as Opalescence and Nu-Pro Gold are also operable with the delivery system of the present invention.

Another oral care product which is operable with the present delivery system is the commercially available fluoride topical gel (1.23%), made by Johnson & Johnson of Skillman, N.J., which is intended for topical application of fluoride to aid in the protection against dental caries.

Strip of material 12 is preferably a 0.013 thick piece of high density polyethylene film. The film preferably has an array of shallow pockets, typically 0.4 mm across and 0.1 mm deep. Strip of material 12 has a flexural stiffness of about 0.6 grams/centimeter as measured on a Handle-O-Meter, model #211-300, available from Thwing-Albert Instrument Co. of Philadelphia, Pa., as per test method ASTM D2923-95. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width.

Flexural stiffness is a material property that is a function of a combination of strip thickness, width, and material modulus of elasticity. In contrast to the low stiffness (and therefore high drape) of preferred strip of material 12, a typical appliance provided by a dentist for an out-of-office bleaching program has a nominal thickness of about 0.6 mm and a flexural stiffness over 300 grams/centimeter, as measured on a Handle-O-Meter per the above ASTM test.

When shallow pockets are included in the strip of material and substances are applied to it in various thicknesses, the overall thickness of the delivery system is preferably less than about 1 millimeter. Thickness of the layer of substance 14 is preferably about 0.4 mm.

Preferably, the delivery system of the present invention is used by applying a tooth whitener to a tooth continuously for 120 minutes a day, once a day, for about 7 to 14 days to achieve a whitening benefit of 1–4 shade guide improvement as measured by VITA LUMIN® Vacuum Farbskala Shade Guides, a product of VITA Zahnfabrik, of BadSackingen, Germany.

For an oral care product, such as fluoride gel, the delivery system of the present invention is used by applying the gel to a tooth and/or adjoining soft tissue continuously for about 4 minutes, once a year, to aid in the prevention of dental caries.

When the wearer removes the strip of material from the tooth and adjoining soft tissue, there may be a residue of substance remaining on the these surfaces. Residual substance may be easily removed by brushing or rinsing.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A delivery system for an oral care substance, wherein said delivery system is substantially unnoticable when worn, comprising:
   a. a strip of material having a flexural stiffness less than about 50 grams/centimeter as measured on a Handle-O-Meter per ASTM test method D2923-95, said strip of material being readily conformable without permanent deformation to a shape of a tooth and its adjoining soft tissue when said delivery system is placed thereagainst; and
   b. an oral care substance applied to said strip of material such that when said delivery system is placed on a surface of said tooth ad its adjoining soft tissue, said substance contacts said surface providing an active onto said surface, said substance also providing adhesive attachment between said strip of material and said surface to hold said delivery system in place for a sufficient time to allow said active to act upon said surface.

2. The delivery system of claim 1 wherein said substance is a gel.

3. The delivery system of claim 1 wherein said substance is a substantially uniform continuous coating on said strip of material.

4. The delivery system of claim 1 wherein said strip of material has shallow pockets on a substance-coated side of said strip of material, said shallow pockets having said substance located therein.

5. The delivery system of claim 1 wherein said strip of material is a piece of high density polyethylene film having a nominal film thickness of about 0.013 mm.

6. The delivery system of claim 1 wherein said strip of material is substantially flat and rectangular in shape with rounded corners, said strip of material including said substance applied thereon having an overall thickness less than about 1 mm.

7. The delivery system of claim 1 wherein said strip of material has a length sufficient to cover a plurality of adjacent teeth while conforming to the curvature of the wearer's mouth and gaps between said plurality of adjacent teeth.

8. A method of delivering an oral care substance to a surface of a tooth and its adjoining soft tissue, said method comprising the steps of:
   a. applying said substance onto a conformable strip of material having a flexural stiffness less than about 50 grams/centimeter as measured on a Handle-O-Meter per ASTM test method D2923-95; and
   b. applying said conformable strip of material with said substance thereon to said surface without permanent deformation of said strip of material such that said substance contacts said surface, said substance providing an active onto said surface, said substance also providing adhesive attachment between said strip of material and said surface to hold said delivery system in place for a sufficient time to allow said active to art upon said surface;
   wherein said delivery system is substantially unnoticeable when worn.

9. The method of claim 8 wherein said substance is a gel.

10. The method of claim 8 wherein said strip of material is a piece of high density polyethylene film having a nominal film thickness of about 0.013 mm.

11. The method of claim 8 wherein said strip of material is substantially flat and rectangular in shape with rounded corners, said strip of material including said substance applied thereon having an overall thickness less than about 1 mm.

12. The method of claim 8 wherein said strip of material has a length sufficient to cover a plurality of adjacent teeth while conforming to the curvature of the wearer's mouth and gaps between said plurality of adjacent teeth.

13. The method of claim 8 wherein said strip of material and said substance are substantially unnoticeable by others when worn.

14. A method of delivering an oral care substance to a surface of a tooth and its adjoining soft tissue, said method comprising the steps of:
   a. applying said substance onto said surface of said tooth and its adjoining soft tissue;
   b. applying a conformable strip of material having a flexural stiffness less than about 50 grams/centimeter, as measured on a Handle-O-Meter per ASTM test method D2923-95, over said substance on said surface permanent deformation of said strip of material, said substance providing an active onto said surface, said substance also providing adhesive attachment between said strip of material and said surface to hold said delivery system in place for a sufficient time to allow said active to act upon said surface;

wherein said delivery system is substantially unnoticeable when worn.

15. The method of claim 14 wherein said substance is a gel.

16. The method of claim 14 wherein said strip of material is a piece of high density polyethylene film having a nominal film thickness of about 0.013 mm.

17. The method of claim 14 wherein said strip of material has a length sufficient to cover a plurality of adjacent teeth while conforming to the curvature of the wearer's mouth and gaps between said plurality of adjacent teeth.

18. The method of claim 14 wherein said strip of material and said substance are substantially unnoticeable by others when worn.

19. A delivery system for an oral care substance, wherein said delivery system is substantially unnoticable when worn, comprising:
   a. a strip of material having a flexural stiffness less than about 0.6 grams/centimeter as measured on a Handle-O-Meter per ASTM test method D2923-95, said strip of material being readily conformable without permanent deformation to a shape of a tooth and its adjoining soft tissue when said delivery system is placed thereagainst; and
   b. an oral care substance applied to said strip of material such that when said delivery system is placed on a surface of said tooth and its adjoining soft tissue, said substance contacts said surface providing an active onto said surface, said substance also providing adhesive attachment between said strip of material and said surface to hold said delivery system in place for a sufficient time to allow said active to act upon said surface.

20. A delivery system for an oral care substance comprising:
   a. a strip of material having a flexural stiffness less than about 50 grams/centimeter as measured on a Handle-O-Meter per ASTM test method D2923-95, said strip of material being readily conformable without permanent deformation to a shape of a tooth and its adjoining soft tissue when said delivery system is placed thereagainst and said strip of material containing an array of shallow pockets; and
   b. an oral care substance applied to said strip of material such that when said delivery system is placed on a surface of said tooth and its adjoining soft tissue, said substance contacts said surface providing an active onto said surface, said substance also providing adhesive attachment between said strip of material and said surface to hold said delivery system in place for a sufficient time to allow said active to act upon said surface.

21. A delivery system for an oral care substance comprising:
   a. a strip of material made of polyethylene; and
   b. an oral care substance applied to said strip of material such that when said delivery system is placed on a surface of said tooth and its adjoining soft tissue, said substance contacts said surface providing an active onto said surface, said substance also providing adhesive attachment between said strip of material and said surface to hold said delivery system in place for a sufficient time to allow said active to act upon said surface.

* * * * *